(12) United States Patent
Moore, II et al.

(10) Patent No.: US 8,476,439 B2
(45) Date of Patent: Jul. 2, 2013

(54) PYRIDINE CLASSICAL CANNABINOID COMPOUNDS AND RELATED METHODS OF USE

(75) Inventors: Bob M. Moore, II, Nesbit, MS (US); Steven Gurley, Memphis, TN (US); Suni Mustafa, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/405,642

(22) Filed: Feb. 27, 2012

(65) Prior Publication Data

US 2012/0220773 A1   Aug. 30, 2012

Related U.S. Application Data

(63) Continuation-in-part of application No. 12/468,773, filed on May 19, 2009, now Pat. No. 8,124,771.

(60) Provisional application No. 61/128,160, filed on May 19, 2008.

(51) Int. Cl.
    *C07D 491/00*   (2006.01)
(52) U.S. Cl.
    USPC .......................................................... 546/89
(58) Field of Classification Search
    USPC .......................................................... 546/89
    See application file for complete search history.

(56) References Cited

U.S. PATENT DOCUMENTS

| 5,397,781 A | 3/1995 | Yanagibashi et al. |
| 7,229,999 B2 | 6/2007 | Hebeisen et al. |
| 2005/0245554 A1 | 11/2005 | Kopka et al. |
| 2006/0247261 A1 | 11/2006 | Eatheron et al. |
| 2007/0129367 A1 | 6/2007 | Eatherton et al. |
| 2007/0167514 A1 | 7/2007 | Moore, II et al. |

OTHER PUBLICATIONS

Snider et al. J. Org. Chem. 1994,59, 8065-8070.*

* cited by examiner

*Primary Examiner* — Nizal Chandrakumar
(74) *Attorney, Agent, or Firm* — Reinhart Boerner Van Deuren s.c.

(57) ABSTRACT

Disclosed are compounds of the formula I:

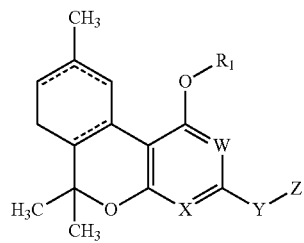

wherein $R_1$, $R_2$, V, W, X, Y and Z can be as defined herein. The compounds can be used in the treatment of disorders mediated by the cannabinoid receptors.

8 Claims, 12 Drawing Sheets

PYRIDINE CLASSICAL CANNABINOID COMPOUNDS AND RELATED METHODS OF USE

This application is a continuation-in-part of and claims priority benefit from application Ser. No. 12/468,773 filed May 19, 2009, now U.S. Pat. No. 8,124,771 issued Feb. 28, 2012 which claims priority from application Ser. No. 61/128,160 filed May 19, 2008, each of which is also incorporated herein by reference in its entirety.

BACKGROUND OF THE INVENTION

The classical cannabinoid, delta-9-tetrahydrocannabinol ($\Delta^9$-THC), is the major active constituent extracted from *Cannabis sativa*. The effects of cannabinoids are due to an interaction with specific high-affinity receptors. Presently, two cannabinoid receptors have been characterized: CB-1, a central receptor found in the mammalian brain and a number of other sites in the peripheral tissues; and CB-2, a peripheral receptor found principally in cells related to the immune system. In addition, it has recently been reported that the GPR35 and GPR55 orphan receptors bind cannabinoid type ligands and have been proposed as third receptor subtypes. The CB-1 receptor is believed to mediate the psychoactive properties associated with classical cannabinoids. Characterization of these receptors has been made possible by the development of specific synthetic ligands such as the agonists WIN 55212-2 (D'Ambra et al., *J. Med. Chem.* 35:124 (1992)) and CP 55,940 (Melvin et al., *Med. Chem.* 27:67 (1984)).

Pharmacologically, cannabinoids can be used to affect a variety of targets such as the central nervous system, the cardiovascular system, the immune system and/or endocrine system. More particularly, compounds possessing an affinity for either the CB-1 or the CB-2 receptors and potentially the GPR35 and GPR55 receptors are useful as anticancer agents, antiobesity agents, analgesics, myorelaxation agents and antiglaucoma agents. Such compounds can also be used for the treatment of thymic disorders, vomiting; various types of neuropathy, memory disorders, dyskinesia, migraine, multiple sclerosis; asthma, epilepsy, ischemia, angor, orthostatic hypotension, osteoporosis, liver fibrosis, inflammation and irritable bowel disease, and cardiac insufficiency.

However, certain cannabinoids such as $\Delta^9$-THC also affect cellular membranes, producing undesirable side effects such as drowsiness, impairment of monoamine oxidase function, and impairment of non-receptor mediated brain function. The addictive and psychotropic properties of some cannabinoids tend to limit their therapeutic value.

There still remains an ongoing need in the art for compounds, whether classical or non-classical cannabinoid analogs, that can be used for therapeutic purposes to affect treatment of conditions or disorders that are mediated by the CB-1 receptor and/or the CB-2 receptor.

SUMMARY OF THE INVENTION

In light of the foregoing, it is an object of the present invention to provide a range of heterocyclic cannabinoid analog compounds, compositions and/or related methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to identify one or more classes of cannabinoid compounds exhibiting affinity for cannabinoid and related receptors found in human cells and tissues.

It can also be an object of the present invention to provide one or more novel pyridine classical cannabinoid receptor ligands, such compounds comprising a pyridine ring system substitution in the A-ring, such compounds as can comprise all known and inferred C3 side chain substitutions together with a hexahydro-, tetrahydro- or non-pyrane ring system.

It can be another object of the present invention to identify such compounds exhibiting cannabinoid receptor selectivity, for directed therapeutic use.

Other objects, features, benefits and advantages of the present invention will be apparent from this summary and the following descriptions of certain embodiments, and will be readily apparent to those skilled in the art having knowledge of various cannabinoid compound and related therapeutic methods. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a cannabinoid analog compound selected from compounds of a formula I below

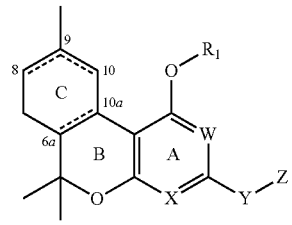

wherein one of W and X can be N and the other can be C; ----- represents an optional double bond wherein the ring that optionally contains it can be selected from hexahydro, 6a,10a-dehydro, 8,9-dehydro, and 9,10-dehydro; Y can be selected from S, O, $CH_2$, $CH(CH_3)$, CH(OH), $C(CH_3)(OH)$, $C(CH_3)_2$, $C(-V(CH_2)_n V-)$, C(O), NH, S(O), and $S(O)_2$; V can be selected from $CH_2$, S and O; n can be an integer $\geq 1$, and preferably from 1 to 6; Z can be selected from H, substituted and unsubstituted alkyl, substituted and unsubstituted cycloalkyl, substituted and unsubstituted aryl, substituted and unsubstituted heteroaryl, substituted and unsubstituted heterocycloalkyl, and arylalkyl, cycloalkylalkyl, heteralkylalkyl and heteroarylalkyl, wherein each alkyl portion can be optionally substituted up to three times and the ring portion of each can be optionally substituted with one, two, three, four or five substituents; and $R_1$ can be selected from H and unsubstituted or substituted alkyl, including but not limited to aminoalkyl, morpholinoalkyl, and hemisuccinate moieties.

In part, the present invention can be directed to a salt of a compound in accordance herewith.

In part, the present invention can be directed to a pro-drug of a compound in accordance herewith.

In part, the present invention can also be directed to a pharmaceutical composition comprising a compound of the sort described herein, a salt and/or a pro-drug thereof, and a pharmaceutically acceptable carrier component.

In part, the present invention can be directed to a method of modifying the activity of a cannabinoid receptor. Such a method can comprise providing a compound, salt and/or pro-drug of the present invention or any other compound disclosed herein that has activity at a cannabinoid or related receptor, a salt and/or pro-drug thereof; and contacting a cell and/or cannabinoid receptor of a cell with such a compound. As illustrated below, such contact can be at least partially sufficient to at least partially modify activity of such a cannabinoid receptor.

In part, the present invention can also be directed to a method of treating a cannabinoid receptor-mediated condition. Such a method can comprise providing a compound in accordance herewith or any other compound disclosed herein that has activity at a cannabinoid receptor, a salt and/or pro-drug thereof; and administering to a patient an amount of such a compound, salt and/or pro-drug, that is at least partially effective to treat a cannabinoid receptor-mediated condition. This aspect of the invention can relate to the use of agonists of a CB-1 or a related receptor, antagonists of a CB-1 or related receptor, agonists of a CB-2 or related receptor, and/or antagonists of a CB-2 or related receptor to treat or prevent disease conditions mediated by hyperactivity of CB-1 and/or CB-2 (or related) receptors or either inactivity or hypoactivity of the CB-1 and/or CB-2 (or related) receptors.

In part, the present invention can also be directed to a compound selected from compounds of a formula

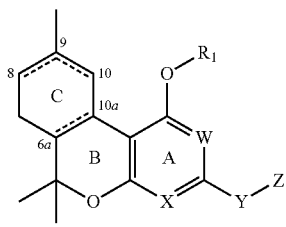

I wherein the C-ring can comprise or be selected from hexahydro-, 6a,10a-dehydro-, 8,9-dehydro- and 9,10-dehydro-structures; $R_1$ can be selected from H, alkyl, aminoalkyl, morpholinoalkyl, and hemisuccinate moieties; Y can be selected from carbonyl, dimethylmethylene and hydroxymethylene moieties; and Z can be selected from substituted and unsubstituted alkyl, phenyl, substituted phenyl, cycloalkyl, substituted cycloalkyl, thiophenyl and substituted thiophenyl moieties, such substituents as would be understood by those skilled in the art made aware of this invention, including but not limited to those described elsewhere herein. In certain embodiments, Z can be an alkyl, phenyl or cycloalkyl moiety and, optionally, Y can be a dimethylmethylene moiety. Regardless, such a compound can be selected from salts and/or pro-drugs of such a compound.

Without limitation, this invention can also be directed to a method of cancer treatment. Such a method can comprise providing a cancer cell comprising a cannabinoid receptor, such a cell of a growth of cancer cells; and contacting such a growth with a cannabinoid compound selected from compounds of a formula I

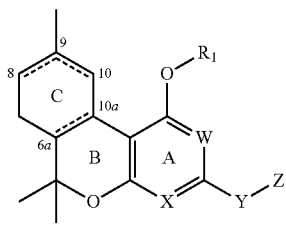

I wherein the C-ring, $R_1$, Y and Z can be as described above. In an embodiment, $R_1$ can be selected from H, alkyl, alkylamino, alkylmorpholino and hemisuccinate moieties; Y can be selected from carbonyl, dimethylmethylene and hydroxymethylene moieties; and Z can be selected from substituted and unsubstituted alkyl, phenyl, substituted phenyl, cycloalkyl, substituted cycloalkyl, thiophenyl and substituted thiophenyl moieties, with such substituents as would be understood by those skilled in the art made aware of this invention, including but not limited to those described elsewhere herein, and salts and pro-drugs of said compounds, and combinations thereof, such compound(s) in an amount at least partially sufficient to induce death of a cell of such a growth. In certain embodiments, Z can be selected from substituted alkyl, unsubstituted alkyl, substituted cycloalkyl, unsubstituted cycloalkyl, phenyl and substituted phenyl moieties, with such substituents as can be selected from chloro, hydroxy and methoxy moieties. In certain such embodiments, $R_1$ can be selected from H and methyl moieties. Regardless, without limitation and as illustrated elsewhere herein, Y can be dimethylmethylene or carbonyl.

DETAILED DESCRIPTION OF CERTAIN EMBODIMENTS

Figure 1:
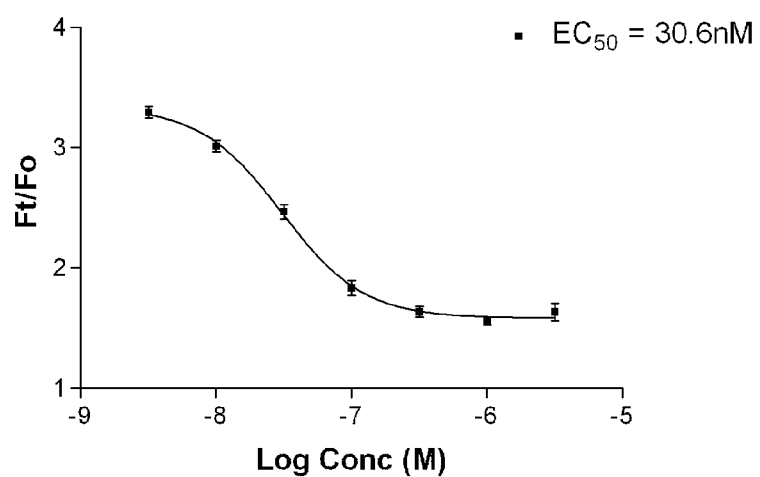
FIG. 1 shows the functional activity of compound 6b at the CB-1 receptor.
Figure 2:
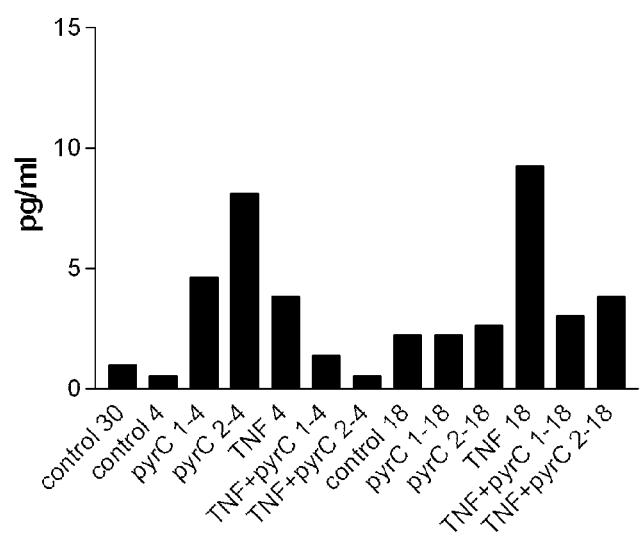
FIG. 2 shows the secretion profiles of G-CSF by A549 cells exposed to compound 6b at the EC1 and EC10 in the presence and absence of TNF-α at 4 and 18 hour intervals.
Figure 3:
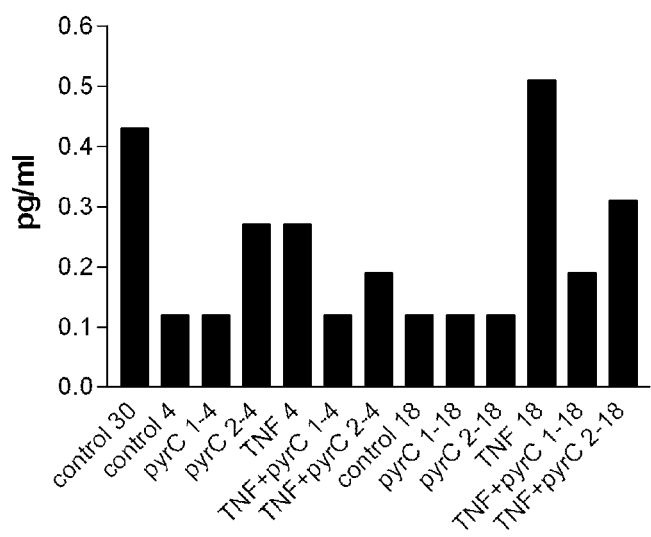
FIG. 3 shows the secretion profiles of IL-1β by A549 cells exposed to compound 6b at the EC1 and EC10 in the presence and absence of TNF-α at 4 and 18 hour intervals.
Figure 4:
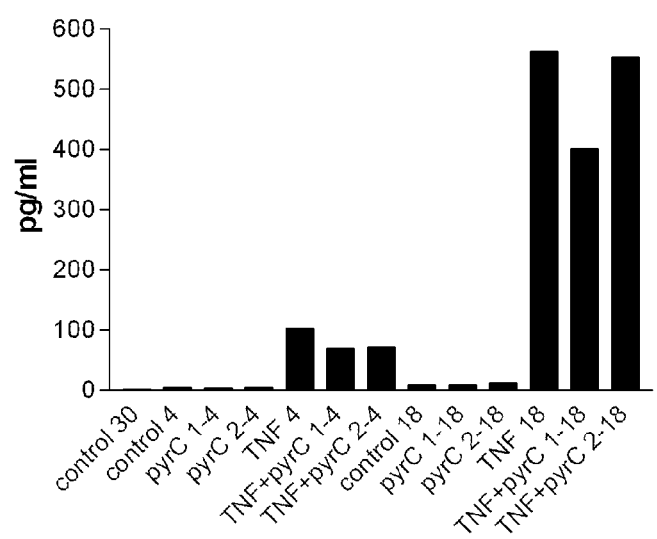
FIG. 4 shows the secretion profiles of IL-6 by A549 cells exposed to compound 6b at the EC1 and EC10 in the presence and absence of TNF-α scaled to show the levels at the 18 hour interval.
Figure 5:
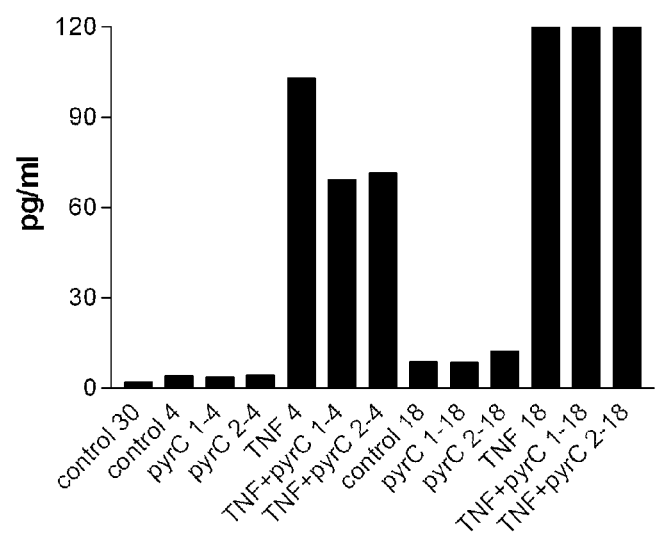
FIG. 5 shows the secretion profiles of IL-6 by A549 cells exposed to compound 6b at the EC1 and EC10 in the presence and absence of TNF-α scaled to show the levels at the 4 hour interval.
Figure 6:
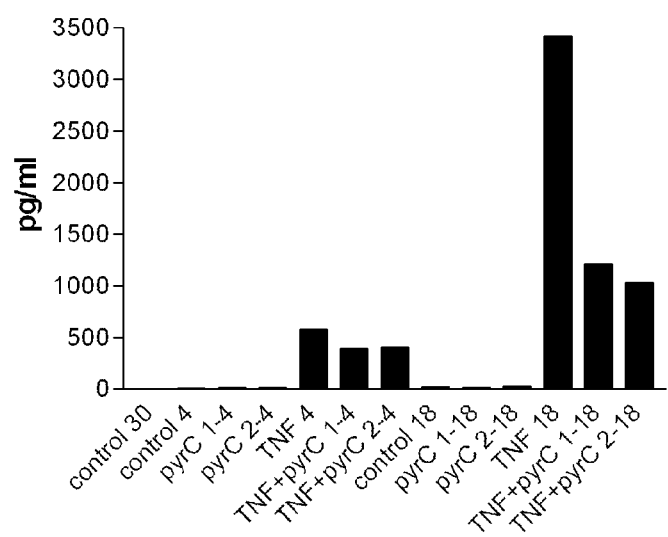
FIG. 6 shows the secretion profiles of IL-8 by A549 cells exposed to compound 6b at the EC1 and EC10 in the presence and absence of TNF-α scaled to show the levels at the 18 hour interval.
Figure 7:
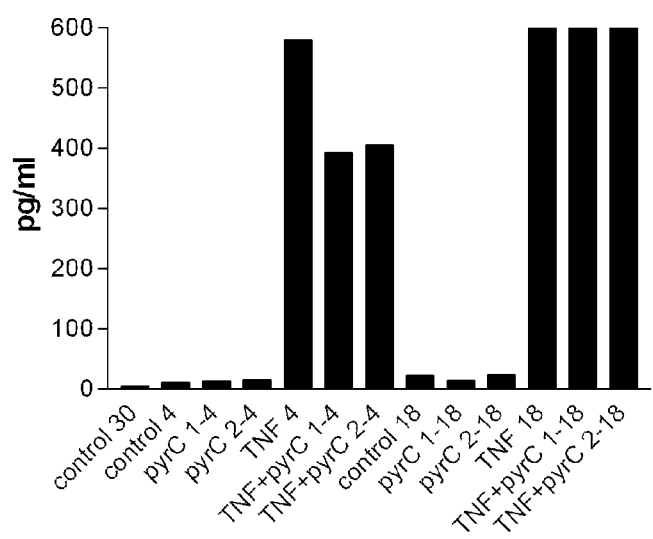
FIG. 7 shows the secretion profiles of IL-8 by A549 cells exposed to compound 6b at the EC1 and EC10 in the presence and absence of TNF-α scaled to show the levels at the 4 hour interval.
Figure 8:
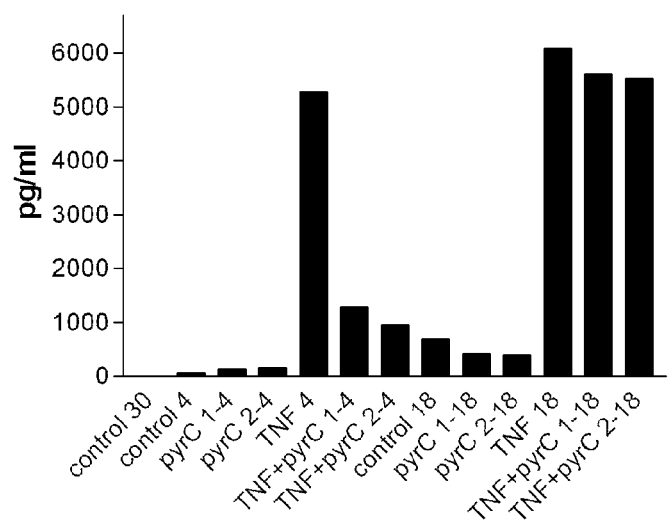
FIG. 8 shows the secretion profiles of MCP-1 by A549 cells exposed to compound 6b at the EC1 and EC10 in the presence and absence of TNF-α at 4 and 18 hour intervals.
Figure 9:
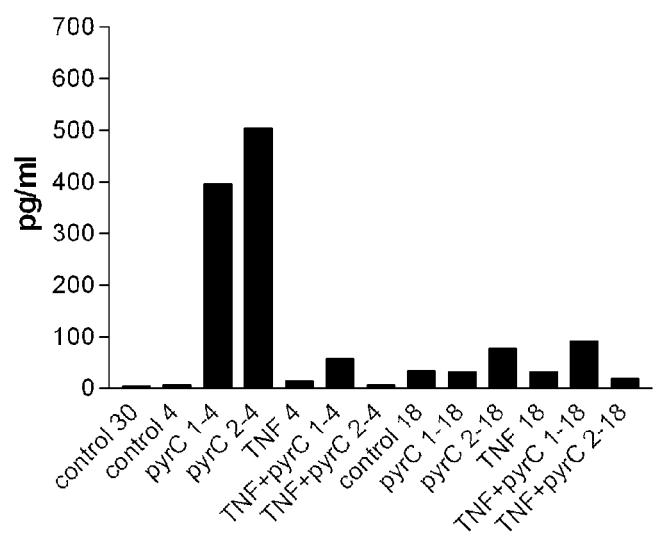
FIG. 9 shows the secretion profiles of MIF by A549 cells exposed to compound 6b at the EC1 and EC10 in the presence and absence of TNF-α scaled to show the levels at the 4 hour interval.
Figure 10:
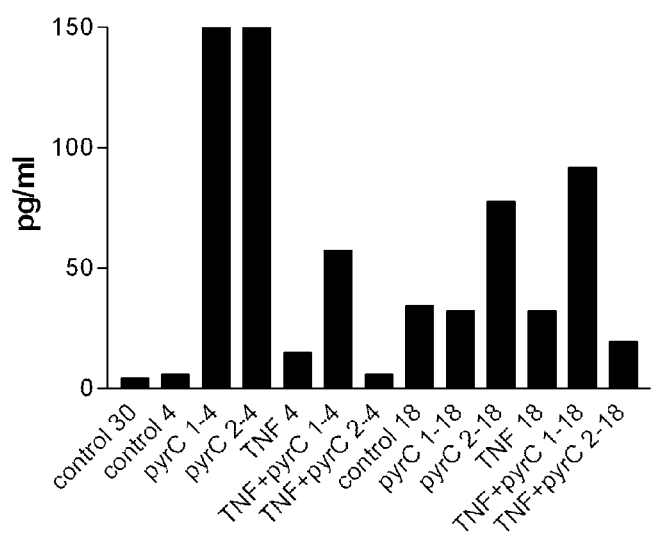
FIG. 10 shows the secretion profiles of MIF by A549 cells exposed to compound 6b at the EC1 and EC10 in the presence and absence of TNF-α scaled to show the levels at the 18 hour interval.
Figure 11:
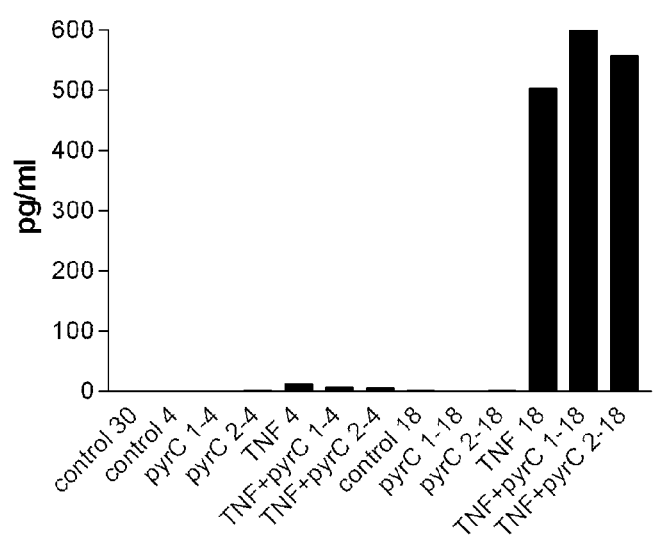
FIG. 11 shows the secretion profiles of RANTES by A549 cells exposed to compound 6b at the EC1 and EC10 in the presence and absence of TNF-α scaled to show the levels at the 18 hour interval.
Figure 12:
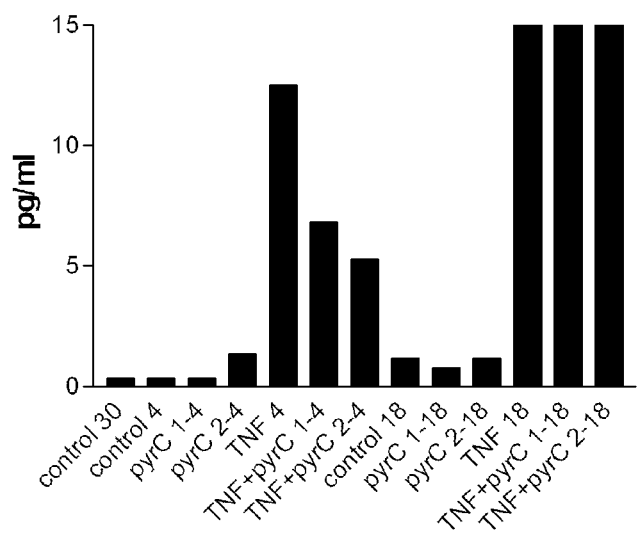
FIG. 12 shows the secretion profiles of RANTES by A549 cells exposed to compound 6b at the EC1 and EC10 in the presence and absence of TNF-α scaled to show the levels at the 4 hour interval.

The novel compounds encompassed by the instant invention are those described by the general Formula I set forth above, and the pharmaceutically acceptable salts and prodrugs thereof.

By "alkyl" in the present invention is meant straight or branched chain alkyl radicals having from 1-20 carbon atoms. Optionally, an alkyl group of the instant invention can contain one or more double bonds and/or one or more triple bonds.

By "cycloalkyl" is meant a carbocyclic radical having from three to twelve carbon atoms. The cycloalkyl can be monocyclic or a polycyclic fused system. Optionally, a cycloalkyl group of the instant invention can contain one or more double bonds and/or one or more triple bonds.

The term "heterocyclyl" refers to one or more carbocyclic ring systems of 4-, 5-, 6- or 7-membered rings which includes fused ring systems and contains at least one and up to four heteroatoms selected from nitrogen, oxygen or sulfur and combinations thereof.

By "aryl" is meant an aromatic carbocyclic ring system having a single ring, multiple rings or multiple condensed rings in which at least one ring is aromatic.

The term "heteroaryl" refers to one or more aromatic ring systems having from three to twelve atoms which includes fused ring systems and contains at least one and up to four heteroatoms selected from nitrogen, oxygen or sulfur and combinations thereof.

By "arylalkyl" is meant an alkyl radical substituted with an aryl, with the the point of attachment is a carbon of the alkyl chain.

As used herein, "substituted" refers to those substituents as would be understood by those skilled in the art. At least one and as many as five substituents can exist on a single group. Examples of such substituents include, but are not limited to, halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl (e.g. trifluoromethyl), carboxy, alkylcarboxy, carbamoyl and the like.

According to one approach, representative, non-limiting pyridine analogs can be prepared by reacting an intermediate pyridine with the appropriate terpine to generate the described C-rings according to the Schemes shown below. The hexahydro is synthesized utilizing a modification of the tandem cyclization method described by Tietz, *Chem. Rev.*, 96:115-136 (1996), and the references cited therein, all incorporated herein by reference in their entirety. The ring formations are accomplished under microwave conditions with the appropriately substituted pyridine and citronellal, either racemic or optically active, as depicted in Scheme 1.

Scheme 1

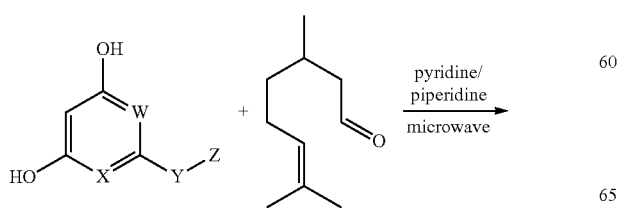

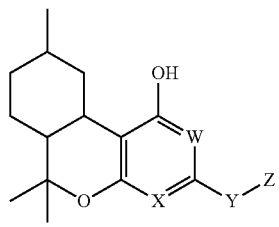

The synthesis of the 9,10- and 8,9-dehydro analogs is accomplished under the same reaction conditions as the hexahydro, however, citronellal is substituted with TBS protected 3-hydroxyl citronellal (Scheme 2). The synthesis of this compound has previously been reported by Kesenheimer and Groth, *Org. Lett.*, 8:2507 (2006), incorporated herein by reference in its entirety.

Scheme 2

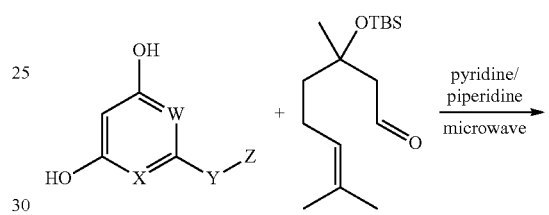

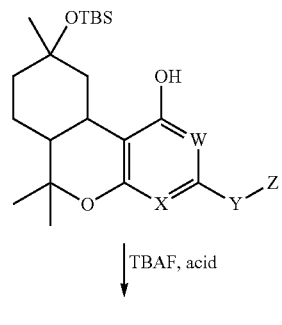

↓ TBAF, acid

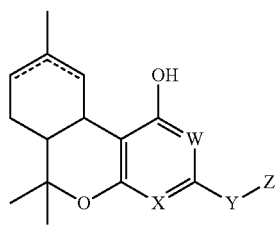

mixture of 8,9- and 9,10-isomers

Synthesis of the 6a,10a-dehydro is accomplished using a method of Adams (U.S. Pat. No. 2,419,934 as incorporated herein by reference in its entirety) utilizing racemic or optically active pulegone and the appropriately substituted pyridine analog (Scheme 3).

Scheme 3

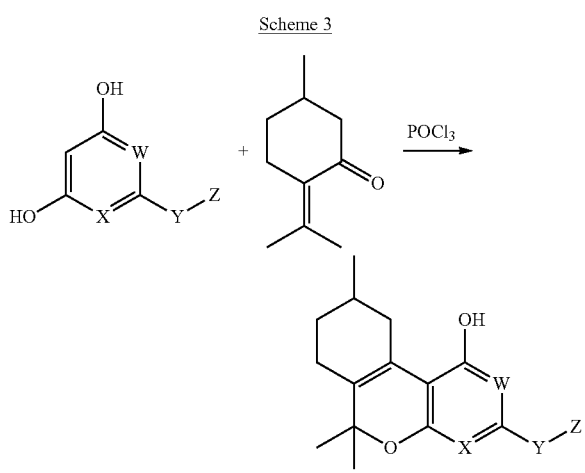

The corresponding pyridines are prepared by reacting dimethyl-, diethyl-, or bis(trichlorophenyl)-malonates with the appropriately substituted Schiff's base derived from the requisite 2-keto analogs, Scheme 4 (See, Ito and Miyajima J., *Heterocycli Chem.*, 29:1037 (1992), and Kappe et al., *J. Heterocyclic Chem.*, 25:463 (1988), each of which is incorporated herein by reference in its entirety), wherein $R_2$ is benzyl or t-butyl and $R_3$ and $R_4$ are methyl, ethyl, phenyl, and/or bis(trichlorophenyl)).

Scheme 4

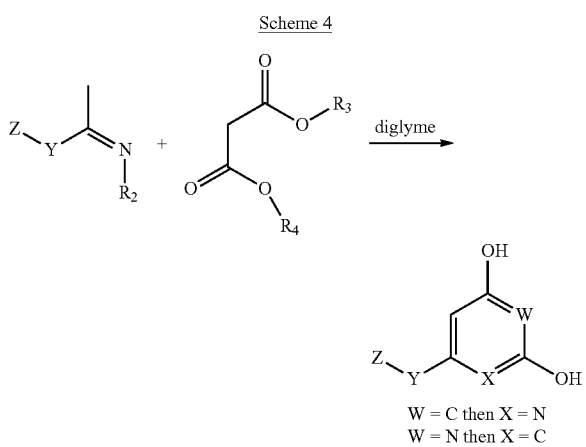

W = C then X = N
W = N then X = C

The requisite substituted 2-keto compounds are either selected from commercially available materials or synthesized from the appropriately substituted nitrile using methyl magnesium bromide or methyl lithium (Scheme 5). Alternatively, the imine formed by the reaction with methyl lithium can be used directly in the formation of the pyridine ring system.

Scheme 5

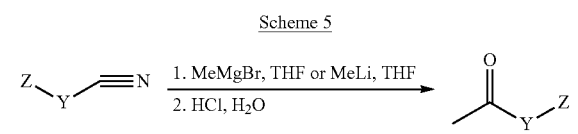

Z = alkyl
 = cycloalkyl
 = heterocycloalky
 = aryl
 = heteroaryl

The starting nitriles are derived from commercially available materials or synthesized using the methods shown in Schemes 6 and 7 which are representative of but not limited to the scope of the chemistry. Derivatives containing a gem-dialkyl, heterocyclic, or carbocyclic substituent at Y, where commercial compounds are not available, are prepared either by direct alkylation of the methylene nitrile (See, U.S. Pat. No. 7,057,076 to Makriyannis and Pub. No. 2004/087590, each of which is incorporated herein by reference in its entirety) or from the appropriately substituted aryl, heteroaryl halogen and isopropyl nitrile.

Scheme 6

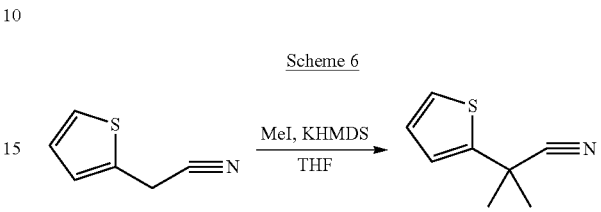

Scheme 7

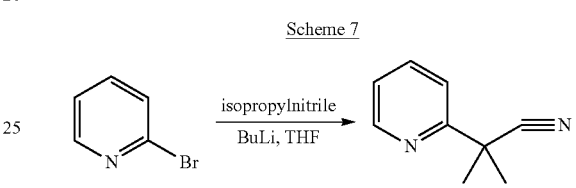

Derivatives containing a keto, hydroxyl, alkylhydroxyl substituent at Y can be prepared by direct oxidation of compounds bearing a Y=$CH_2$ or from the C2-aldehyde pyridine, prepared from bis-ethylsulfanyl-acetaldehyde (Scheme 8) using chemistry previously reported in U.S. Pat. No. 7,169,942, the entirety of which is incorporated herein by reference.

Scheme 8

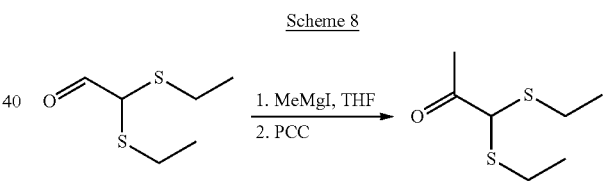

While syntheses of several representative, non-limiting compounds are described herein, it will be understood by those skilled in the art that various other compounds can be prepared using similar such procedures and/or straight-forward modifications thereof. Accordingly, the identities of moieties $R_1$, Y and Z are limited only by the respective reagents, starting materials, intermediates and chemistry thereon.

Likewise, the present invention contemplates, more broadly, various other such compounds, salts and/or pro-drugs thereof, together with corresponding pharmaceutical compositions thereof, as also described in the aforementioned co-pending application. Such compounds, salts, pro-drugs and/or pharmaceutical compositions can be used as described therein. For instance, the present invention can be used to modify the activity of one or both of the CB-1 and CB-2 receptors. Such a method can be carried out by contacting a cell and/or cannabinoid receptor thereof with a compound of the present invention, such contact at least partially sufficient to at least partially modify the activity of such a cannabinoid receptor, whether ex vivo or in vivo.

More generally, various physiological and/or therapeutic advantages of the present compounds and/or compositions can be realized with consideration of the authorities cited in the aforementioned co-pending application. The inventive analogs, as described herein, can be administered in therapeutically-effective amounts to treat a wide range of indications. Without limitation, various such conditions and/or disease states are described in paragraph 0067 of co-pending application Ser. No. 12/074,342, filed Mar. 3, 2008 and entitled "Tri-Aryl/Heteroaromatic Cannabinoids and Use Thereof," the entirety of which is incorporated herein by reference.

Accordingly, this invention can be directed to a method comprising providing a compound of the sort described herein, such a compound exhibiting activity at a cannabinoid receptor; and contacting a cell comprising a cannabinoid receptor with such a compound and/or administering such a compound to a patient, such a compound in an amount at least partially effective to treat a cannabinoid receptor/mediated condition. Such a cannabinoid receptor can be a receptor described herein or as would otherwise be understood or realized by those skilled in the art made aware of this invention.

The activity of cannabinoid and related receptors can be affected, mediated and/or modified by contacting such a receptor with an effective amount of one or more of the present compounds as can be present in or as part of a pharmaceutical composition or treatment, or by contacting a cell comprising such a receptor with an effective amount of one or more such compounds, so as to contact such a receptor in the cell therewith. Contacting may be in vitro or in vivo. Accordingly, as would be understood by those skilled in the art, "contact" means that a cannabinoid and/or related receptor and one or more compounds are brought together for such a compound to bind to or otherwise affect or modify receptor activity. Amounts of one or more such compounds effective to modify and/or affect receptor activity can be determined empirically and making such a determination is within the skill in the art.

Without limitation, analog compounds of this invention can be used ex vivo in receptor binding assays of the sort described in Example 2 of the aforementioned co-pending '342 application. In vitro activity of the present analog compounds can be demonstrated in a manner similar to that described in Example 3 of the co-pending application. Alternatively, in vivo activity can be demonstrated using the protocols described in Examples 4 and 6, thereof. More specifically, anti-cancer activity of various representative compounds of this invention can be shown against human lung, prostate, colorectal and pancreatic cancer cell lines using the methodologies described in Example 9 of the aforementioned co-pending '342 application. Extending such a methodology, the present invention can also be used to treat cancer growth of the central nervous system and/or induce cellular death within such growth. In accordance with this invention, various cannabinoid compounds of the sort described herein, including but not limited to those discussed above, can also be used in conjunction with a method to treat human glioma and/or brain cancers. Illustrating such embodiments, one or more compounds of the present invention can be provided and used, as described in the co-pending application, to contact and/or treat human brain cancers, such contact and/or treatment as can be confirmed by cell death and/or related effects.

EXAMPLES OF THE INVENTION

The following non-limiting examples and data illustrate various aspects and features relating to the compounds, compositions and/or methods of the present invention, including the synthesis of pyridine classical cannabinoid receptor ligands and/or compounds, as are available though the methodologies described herein. In comparison with the prior art, the present compounds and methods provide results and data which are surprising, unexpected and contrary thereto. While the utility of this invention is illustrated through the preparation and use of several compounds, moieties and/or substituents thereof, it will be understood by those skilled in the art that comparable results are obtainable with various other compounds, moieties and/or substituents, as are commensurate with the scope of this invention. All compounds are named using ChemBioDraw Ultra Version 11.0.01.

Example 1a

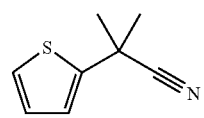

1a

2-Methyl-2-(thiophen-2-yl)propanenitrile—To a solution of 2-(thiophen-2-yl) acetonitrile (1 g, 8.13 mmol) in 4 ml anhydrous THF, KHMDS (24.4 mmol, 48.9 ml, 0.5M in toluene) was added at 0° C. The mixture was allowed to stir for 3 minutes, after which a solution of 16.26 mmol iodomethane (1.13 ml in 26 ml anhydrous THF) was added slowly over a period of 10 minutes. The mixture was stirred for 5 minutes and monitored by TLC. Upon completion, the reaction was quenched with aqueous ammonium chloride. The organic phase was separated with ethyl acetate and dried over sodium sulfate. The product was purified via vacuum distillation. (bp 42° C. at 1 torr) Yield: 89%. $^{1}$H NMR (500 MHz, CDCl$_3$): δ (ppm) 7.4 ppm (d, 1H), 7.2 ppm (t, 1H), 7.0 ppm (d, 1H), 1.9 ppm (s, 6H).

Example 1b

In a similar fashion the following compound was synthesized.

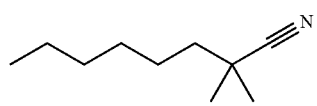

1b 2,2-Dimethyloctanenitrile—Purified via vacuum distillation (bp 50-55° C. at 1.1 torr). Yield: 84% I.R. (neat) nitrile 2230 cm$^{-1}$, $^{1}$H NMR (500 MHz, CDCl$_3$): δ (ppm) 1.5 ppm (m, 4H). 1.4-1.3 ppm (m, 12H), 0.9 ppm (s, 3H).

Example 2a

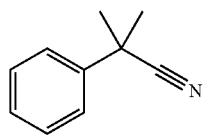

2a

2-Methyl-2-phenylpropanenitrile—To a solution of fluorobenzene (5.85 mL, 62 4 mmol) in 100 mL of anhydrous toluene was added isobutyronitrile (22.5 mL, 250 mmol) followed by 200 mL (100 mmol) of a 0.5 M solution of KHMDS in toluene. The reaction was stirred at 80° C. for 24 hours. The reaction was then allowed to cool to room temperature, diluted with diethyl ether, and washed with water and brine. The organic fraction was dried over sodium sulfate and concentrated under reduced pressure. The product was purified by flash chromatography using an ethyl acetate/hexanes gradient to yield 4.57 g (50%) of the objective compound as a brown oil. MS: (ESI, Pos) m/z 168.0 (M+23) $^1$H NMR (500 MHz, CDCl$_3$): δ (ppm) 7.48 (d, 2H), 7.39 (t, 2H), 7.31 (t, 1H), 1.73 (s, 6H).

Example 2b

In a similar fashion the following compound was synthesized.

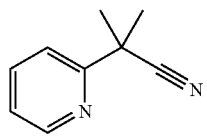

2b

2-Methyl-2-pyridin-2-yl-propanenitrile—Purified in a manner similar to 2-methyl-2-phenylpropanenitrile 2a using 2-bromopyridine as the starting material to yield a brown oil. MS: (ESI, Pos) m/z 168.9 (M+23).

Example 3a

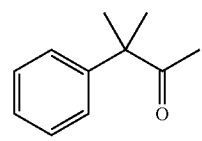

3a

3-Methyl-3-phenylbutan-2-one—To a solution of 2-methyl-2-phenyl-propanenitrile (2a, 500 mg, 3 1 mmol) in anhydrous THF cooled to 0° C. was added methyl magnesium bromide (408 mg, 3.4 mmol). The reaction was warmed to room temperature and then refluxed overnight. The mixture was treated with 1N HCl and the aqueous phase extracted with diethyl ether. Product was confirmed by MS: (ESI, Pos) m/z 187.2 (M+23).

Example 3b

Various other ketones can be prepared from the respective nitriles, using synthetic procedures comparable to those described above, to provide the corresponding Schiffs base components en route to the Y- and/or Z-substituted pyridine intermediates, as illustrated below.

Example 4

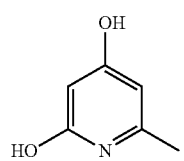

4

6-Methylpyridine-2,4-diol—A solution of acetone (1 g, 17 2 mmol) and benzylamine (1.7 g, 16 3 mmol) in benzene (40 mL) was added 4 g of powdered molecular sieves and the reaction was stirred at room temperature overnight. The sieves were filtered, the solvent removed under reduced pressure, and the resulting residue was purified by column chromatography. The imine is dissolved in diglyme to which 1.2 equivalents of dialkyl or diaryl malonate was added and the mixture refluxed for 24 hours. The product was separated by column chromatography.

Example 5

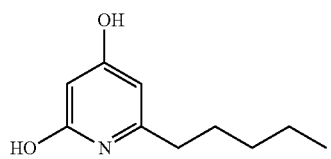

5

6-Pentylpyridine-2,4-diol—Into a round bottomed flask fitted with a Dean-Stark trap and condensor was added a solution of 2-heptanone (1 g, 8 7 mmol) and benzylamine (0.9 g, 8.3 mmol) in benzene (40 ml). The mixture was refluxed overnight yielding approxiamtely 0.1 mL of water (64% yield of the imine based on colllected water). The solvent was removed and the imine purified by column chromatograph. The imine is dissolved in diglyme to which 1.2 equivalents of dialkyl or diaryl malonate was added and the mixture refluxed for 24 hours. The product was separated by column chromatography.

Example 6a

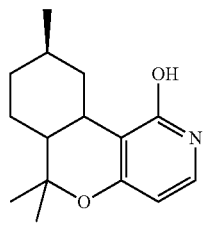

6a (9R)-6,6,9-trimethyl-6a,7,8,9,10,10a-hexahydro-6H-isochromeno[4,3-c]pyridin-1-ol (6a)—Pyridine-2,4-diol (4, 80 mg, 0.72 mmol) was added to 4 mL of absolute ethanol in a 10 mL microwave reaction vessel. To this was added 89 μL of pyridine and 4 μL of piperidine followed by 390 μL (2.16 mmol) of (R)-(+)-citronellal. The reaction vessel was then sealed and irradiated at 200 watts to 130° C. for 1 hour. The solvent was then removed by rotary evaporation and the product purified by flash chromatography using a methanol/methylene chloride gradient to yield 76 mg (63%) of the objective product 6a as a light yellow solid. MS: (ESI, Pos) m/z 248.0 (M+1) $^1$H NMR (500 MHz, CDCl$_3$): δ (ppm) 11.99 (br.s, 1H), 7.11 (d, 1H), 5.84 (d, 1H), 3.33 (d, 1H), 2.34 (m, 1H), 1.83 (m, 2H), 1.63 (m, 2H), 1.38 (s, 3H), 1.26 (m, 1H), 1.09 (s, 3H), 1.03 (m, 1H), 0.94 (d, 3H), 0.58 (q, 1H) $^{13}$C NMR (500 MHz, CDCl$_3$): δ (ppm) 165.73, 162.95, 132.42, 110.29, 101.93, 79.53, 48.64, 37.25, 35.68, 34.71, 32.58, 27.96, 27.57, 22.68, 19.49.

Example 6b

In a similar fashion the following compounds were synthesized.

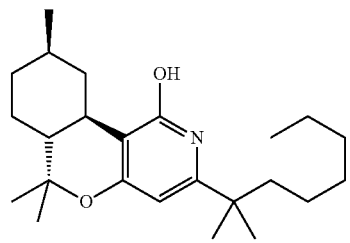

(6aS,9R,10aR)-6,6,9-trimethyl-3-(2-methyloctan-2-yl)-6a,7,8,9,10,10a-hexahydro-6H-isochromeno[4,3-c]pyridin-1-ol (6b) Off white waxy solid, Yield: 38% MS: (ESI, Pos.) 372.10 (M−1) ¹HNMR (300 MHz, DMSO-d6): ∂(ppm) 8.6 (s, 1H), 6.5 (s, 1H), 2.91 (m, 1H), 2.49 (m, 1H), 2.31 (m, 2H), 1.28-1.33 (m, 10H), 1.04-1.23 (m, 14H), 0.99-1.02 (m, 3H), 0.89 (d, 3H), 0.83 (t, 3H).

Example 6c

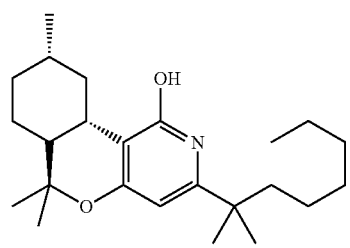

(6aR, 9S, 10aS)-6,6,9-trimethyl-3-(2-methyloctan-2-yl)-6a,7,8,9,10,10a-hexahydro-6H-isochromeno[4,3-c]pyridin-1-ol (6c) This compound was synthesized by substituting (R)-(+)-citronellal with (S)-(−)-citronellal. Off white waxy solid, Yield: 36% MS: (ESI, Pos.) 372.20 (M−1) ¹HNMR (300 MHz, CDCl₃): ∂(ppm) 6.2 (s, 1H), 3.1 (m, 1H), 2.43 (m, 1H), 1.28-2.10 (m, 12H), 1.04-1.23 (m, 14H), 0.99-1.02 (m, 3H), 0.91 (d, 3H), 0.83 (t, 3H).

Example 6d

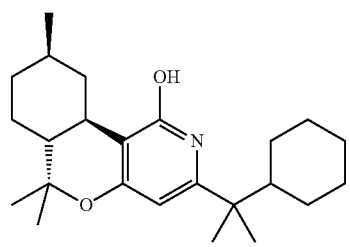

(6aS, 9R, 10aR)-3-(2-cyclohexylpropan-2-yl)-6,6,9-trimethyl-6a,7,8,9,10,10a-hexahydro-6H-isochromeno[4,3-c]pyridin-1-ol (6d)—Off white waxy solid, Yield: 33% MS: (ESI, Pos.) 370.20 (M−1) ¹HNMR (500 MHz, CDCl₃): ∂(ppm) 7.37 (s, 1H), 6.0 (s, 1H), 3.41 (d, 1H), 2.38 (t, 1H), 1.53-1.85 (m, 13H), 1.43-1.15 (m, 9H), 1.08-1.02 (m, 8H), 0.92 (d, 3H).

Example 6e

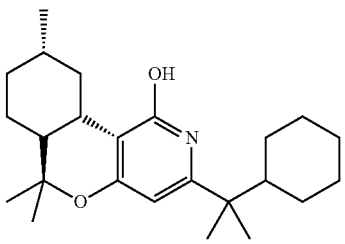

(6aR, 9S, 10aS)-3-(2-cyclohexylpropan-2-yl)-6,6,9-trimethyl-6a,7,8,9,10,10a-hexahydro-6H-isochromeno[4,3-c]pyridin-1-ol (6e)—Off white waxy solid, Yield:31% MS: (ESI, Neg) 370.1 (M−1) ¹HNMR (300 MHz, CDCl₃): ∂(ppm) 7.48(s,1H), 6.04(s,1H), 3.43(d,1H), 2.41 (t,1H), 1.52-1.88 (m,13H), 1.43-1.15(m,8H), 1.08-1.02(m,8H), 0.94 (d,3H), 0.65(q,1H).

Example 6f

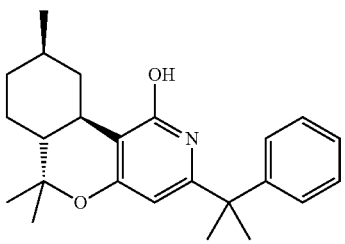

(6aS, 9R, 10aR)-6,6,9-trimethyl-3-(2-phenylpropan-2-yl)-6a,7,8,9,10,10a-hexahydro-6H-isochromeno[4,3-c]pyridin-1-ol (6f)—white powder, Yield:52% MS: (ESI, Neg) 364.1 (M−1) ¹HNMR (300 MHz, CDCl₃): ∂(ppm) 7.79 (bs,1H), 7.28(m,5H), 5.89(s,1H), 3.21(m,1H), 2.31 (m,1H), 1.85(m,1H),1.60-1.62(m,9H), 1.4 (s,6H), 1.18(m,2H), 0.95(d,3H), 0.61(q,1H).

Example 6g

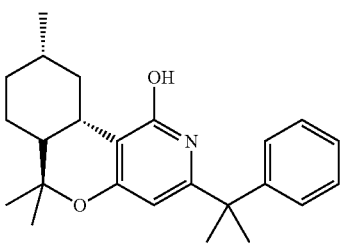

(6aR, 9S, 10aS)-6,6,9-trimethyl-3-(2-phenylpropan-2-yl)-6a,7,8,9,10,10a-hexahydro-6H-isochromeno[4,3-c]pyridin- 1-ol (6g)—white powder, Yield:44% MS: (ESI, Neg) 364.0 (M−1) $^1$HNMR (300 MHz, CDCl$_3$): ∂(ppm) 7.41(m,5H), 7.1 (bs,1H), 6.12(s,1H), 3.39(m,1H), 2.41 (m,1H), 1.89(m,1H), 1.62-1.63(m,9H), 1.43 (s,6H), 1.20(m,2H), 0.99(d,3H), 0.65 (q,1H).

Example 7

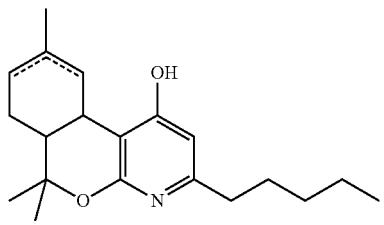

7

6,6,9-Trimethyl-3-pentyl-tetrahydro-6H-isochromeno[3,4-b]pyridin-1-ol—The material was synthesized from 6-pentylpyridine-2,4-diol 5 and TBS protected 3-hydroxyl citronella (Kesenheimer and Groth, *Org. Lett.*, 8:2507 (2006)) as described above. The TBS protecting group was removed using TBAF and the compound was dehydrated employing a general acid to yield a mixture of separable isomers.

Example 8

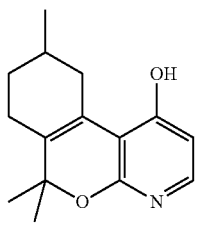

8

6,6,9-Trimethyl-7,8,9,10-tetrahydro-6H-isochromeno[3,4-b]pyridin-1-ol (8)—Pyridine-2,4-diol (4, 100 mg, 0 9 mmol) was added to 3 mL of absolute ethanol in a 10 mL microwave reaction vessel. To this was also added 66 μL of pyridine and 3 μL of piperidine followed by 0.46 g (3 mmol) of (R)-(+)-pulegone. The reaction vessel was then sealed and irradiated at 300 watts to 130° C. for 1 hour. The solvent was then removed by rotary evaporation and the product purified by flash chromatography using a methanol/methylene chloride gradient to yield a light yellow solid. MS: (ESI, Neg) m/z 244.9 (M−1).

Example 9

While several compounds with tetrahydro and dehydro C-ring structures are shown, other such compounds can be prepared to provide a range of Y- and/or Z moieties, such compounds limited only by the commercial or synthetic availability of the corresponding pyridine and terpine intermediates. Likewise, R$_1$ can be varied depending on choice of starting material or subsequent chemistry on the resulting cannabinoid compound.

Example 10

Receptor Binding Assays

Cell membranes from HEK293 cells transfected with the human CB-1 receptor and membranes from CHO-K1 cells transfected with the human CB-2 receptor were prepared. [$^3$H]CP 55,940 having a specific activity of 120 Ci/mmol was obtained from Perkin-Elmer Life Sciences, Inc. All other chemicals and reagents were obtained from Sigma-Aldrich. The assays were carried out in 96 well plates obtained from Millipore, Inc. fitted with glass fiber filters (hydrophilic, GFC filters) having a pore size of 1.2μ. The filters were soaked with 0.05% polyethyleneimine solution and washed 5× with deionized water prior to carrying out the assays. The filtrations were carried out on a 96 well vacuum manifold (Millipore Inc.), the filters punched out with a pipette tip directly into scintillation vials at the end of the experiment, and the vials filled with 5 ml scintillation cocktail Ecolite (+) (Fisher Scientific). Counting was carried out on a Beckmann Scintillation Counter model LS6500. Drug solutions were prepared in DMSO and the radioligand was dissolved in ethanol.

Incubation buffer: 50 mM TRIS-HCl, 5 mM MgCl$_2$, 2.5 mM EDTA, 0.5 mg/ml fatty acid free bovine serum albumin, pH 7.4.

Binding protocol for the CB-1 receptor: 8 μg of membranes (20 μl of a 1:8 dilution in incubation buffer) was incubated with 5 μl of drug solution ($10^{-4}$M to $10^{-12}$M) and 5 μl of 5.4 nM [$^3$H]CP 55,940 in a total volume of 200 μl for 90 mins at 30° C. Non-specific binding was determined using 10 μM WIN55,212-2 (K$_i$=4.4 nM). The membranes were filtered and the filters washed 7× with 0.2 ml ice-cold incubation buffer and allowed to air dry under vacuum.

Binding protocol for the CB-2 receptor: 15.3 μg of membranes (20 μl of a 1:20 dilution in incubation buffer) was incubated with 5 μl of drug solution ($10^{-4}$M to $10^{-12}$M) and 5 μl of 10 nM [$^3$H]CP 55,940 in a total volume of 200 μl for 90 minutes at 30° C. Non-specific binding was determined using 10 μM WIN55,212-2 (K$_i$=4.4 nM). The membranes were filtered and the filters washed 7× with 0.2 ml ice-cold incubation buffer and allowed to air dry under vacuum.

Data accumulation and statistical analysis: Varying concentrations of drug ranging from $10^{-4}$M to $10^{-12}$M were added in triplicate for each experiment and the individual molar IC$_{50}$ values were determined using GraphPad Prism. The corresponding K$_i$ values for each drug were determined utilizing the Cheng and Prusoff equation and final data was presented as K$_i$±S.E.M. of n≧2 experiments.

Functional assays: HEK-293 cell lines stably transfected with a cyclic nucleotide-gated channel and either human CB-1 or CB-2 receptors (BD Biosciences, San Jose, Calif. USA) were seeded in poly-D-lysine coated 96-well plates at a density of 70,000 cells per well. Plates were incubated at 37° C. in 5% CO$_2$ overnight prior to assay. Plates were then removed from the incubator and the complete growth medium (DMEM, 10% FBS, 250 ‖g/ml G418 and 1 μg/ml puromycin) was replaced with 100 μL DMEM containing 0.25% BSA. Next, 100 μL membrane potential dye loading buffer (Molecular Devices, Sunnyvale, Calif. USA) was prepared according to the manufacturer. The plates were placed back into the incubator for 30 minutes and then the baseline fluorescence was read on a BioTek Synergy 2 multi-mode microplate reader (BioTek Instruments, Winooski, Vt. USA) with 540 nm excitation and 590 nm emission filters prior to drug addition. Drugs were added in 50 μL DPBS containing 2.5% DMSO, 1.25 μM 5'-(N-ethylcarboxamido) adenosine and 125 μM Ro 20-1724. Plates were then incubated at room temperature for 25 minutes and fluorescence measured again at 540 nm excitation and 590 nm emission.

FIG. 1 depicts the functional activity of compound 6b at the CB-1 receptor.

Cytoxocity assay: Cells were seeded on a 96 well polystyrene plate in full serum media at a density of 75,000 cells per milliliter, 100 μL per well. Plates were incubated at 37° C. and 5% CO₂ for 24 hours to allow cell attachment. Drug solutions were prepared in DMSO at 100× concentration and mixed 1:100 in 1% FBS media to yield the desired concentration. Drug-media mixtures were vortexed immediately prior to administration to cells. Full serum media was removed and replaced with drug-media mixtures and incubated for 18 hours. 10 μL of Cell Counting Kit 8 (CCK8, Dojindo# CK04-11) was added to each well to colormetrically assess viability. After 2-4 hours of incubation with the CCK8 dye, absorbance was read at 450 nm by a BioTek Synergy 2 plate reader.

The cytotoxicity of selected compounds against the glioblastoma brain cancer cell line LN-229 is depicted in Table 1.

TABLE 1

| Compound | EC$_{50}$ (μM) |
|---|---|
| 6b | 2.43 |
| 6c | 1.83 |

Inflammation Studies

Differentiation of Monocytes: To THP-1 human leukemia monocytes (ATCC #TIB-202) in suspension was added phorbol 12-myristate 13-acetate (PMA Aldrich #P1585) and ionomycin (Aldrich #I0634), 10 and 500 ng/ml respectively, to induce differentiation into macrophage-like cells. Cells were seeded at 30,000 cells/well and allowed to incubate at 37° C. in 5% CO₂/95% air for 3-10 days to complete transformation. Media was refreshed as needed until assay.

Cytokine Assay: A549 (ATCC #CCL-185), HUV-EC-C (ATCC #CRL-1730), or differentiated THP-1 cells were seeded on 96-well polystyrene plates at a density of 300,000 cells/ml (100 μL per well) and incubated at 37° C. in 5% CO₂/95% air for 24 hours to allow cell attachment. Drug solutions were prepared in DMSO at 100× concentration and mixed 1:100 in 1% FBS media to yield the desired concentration.

Plates were then removed from the incubator and the complete growth media was replaced with 50 μL media containing 1% FBS and lipopolysaccharide or peptidoglycan at 1 μg/ml (for differentiated THP-1), or TNF-α (10 ng/ml) or IL-1β (1 ng/ml) in the case of A549 and HUVEC or without stimulus in the case of control wells. Cells were returned to the incubator for 1 hour before drug treatments. Drug-media solutions were prepared at 2× desired final concentration in media containing 1% FBS and the appropriate stimulus at the previously mentioned concentration. Control media was also prepared which contained no drug. 50 μL of drug containing media or control was then added to appropriate wells and the plates returned to the incubator for 18 hours. Media supernatants were then removed from the wells and frozen at −80° C. until time of assay.

FIGS. 2-12 depict secretion profiles of various modulators by A549 exposed to compound 6b at the EC1 and EC10 in the presence and absence of TNF-α at 4 and 18 hour intervals. The graph legends are as follows: pyrC 1-4=6b at 1.1 μM for 4 hours; pyrC 2-4=6b at 1.6 μM for 4 hours; pyrC 1-18=6b at 1.1 μM for 18 hours; pyrC 2-18=6b at 1.6 μM for 18 hours; TNF=TNF-α at 10 ng/ml.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What is claimed is:

1. A compound of the formula

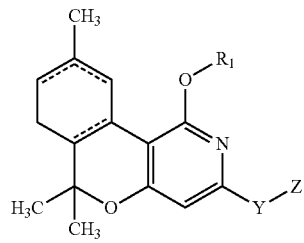

wherein:
- - - - - represents an optional double bond wherein the ring that optionally contains it is selected from hexahydro, 6a,10a-dehydro, 8,9-dehydro, and 9,10-dehydro;

Y is selected from CH₂, CH(CH₃), CH(OH), C(CH₃)(OH), C(CH₃)₂, C(—U(CH₂)ₙU—) and C(O);

n is an integer ≧1;

U is CH₂;

Z is selected from H, substituted and unsubstituted alkyl, and cycloalkyl, cycloalkylalkyl, aryl, arylalkyl, heteroaryl, heteroarylalkyl, heterocycloalkyl, and heterocycloalkylalkyl, wherein each alkyl portion is optionally substituted up to three tunes and the ring portion of each is optionally substituted with one, two, three, four or five substituents; and R₁ is selected from H and substituted and unsubstituted alkyl.

2. A compound according to claim 1 wherein
Y is selected from carbonyl, dimethylmethylene and hydroxymethylene; and
Z is selected from substituted or unsubstituted alkyl, substituted or unsubstituted cycloalkyl, substituted or unsubstituted phenyl, and substituted or unsubstituted thiophenyl.

3. A compound according to claim 2 wherein Z is alkyl, cycloalkyl or phenyl.

4. A compound according to claim 3 wherein Z is hexyl, cyclohexyl or phenyl.

5. A compound according to claim 2 wherein Y is dimethylmethylene.

6. A compound according to claim 1 selected from
(6aS, 9R, 10aR)-6,6,9-trimethyl-3-(2-methyloctan-2-yl)-6a,7,8,9,10,10a-hexahydro-6H-isochromeno[4,3-c]pyridin-1-ol;
(6aR, 9S, 10aS)-6,6,9-trimethyl-3-(2-methyloctan-2-yl)-6a,7,8,9,10,10a-hexahydro-6H-isochromeno[4,3-c]pyridin-1-ol;
((6aS, 9R, 10aR)-3-(2-cyclohexylpropan-2-yl)-6,6,9-trimethyl-6a,7,8,9,10,10a-hexahydro-6H-isochromeno[4,3-c]pyridin-1-ol;
(6aR, 9S, 10aS)-3-(2-cyclohexylpropan-2-yl)-6,6,9-trimethyl-6a,7,8,9,10,10a-hexahydro-6H-isochromeno[4,3-c]pyridin-1-ol;
(6aS, 9R, 10aR)-6,6,9-trimethyl-3-(2-phenylpropan-2-yl)-6a,7,8,9,10,10a-hexahydro-6H-isochromeno[4,3-c]pyridin-1-ol; and
(6aR, 9S, 10aS)-6,6,9-trimethyl-3-(2-phenylpropan-2-yl)-6a,7,8,9,10,10a-hexahydro-6H-isochromeno[4,3-c]pyridin-1-ol.

7. A pharmaceutical composition comprising a compound of claim 1.

8. A pharmaceutical composition of claim 7 wherein the compound is selected from the group consisting of (6aS, 9R, 10aR)-6,6,9-Trimethyl-3-(2-methyloctan-2-yl)-6a,7,8,9,10,10a-hexahydro-6H-isochromeno[3,4-b]pyridin-1-ol;

(6aR, 9S, 10aS)-6,6,9-Trimethyl-3-(2-methyloctan-2-yl)-6a,7,8,9,10,10a-hexahydro-6H-isochromeno[3,4-b]pyridin-1-ol;

((6aS, 9R, 10aR)-3-(2-Cyclohexylpropan-2-yl)-6,6,9-trimethyl-6a,7,8,9,10,10a-hexahydro-6H-isochromeno[3,4-b]pyridin-1-ol;

(6aR, 9S, 10aS)-3-(2-Cyclohexylpropan-2-yl)-6,6,9-trimethyl-6a,7,8,9,10,10a-hexahydro-6H-isochromeno[3,4-b]pyridin-1-ol;

(6aS, 9R, 10aR)-6,6,9-Trimethyl-3-(2-phenylpropan-2-yl)-6a,7,8,9,10,10a-hexahydro-6H-isochromeno[3,4-b]pyridin-1-ol; and (6aR, 9S, 10aS)-6,6,9-Trimethyl-3-(2-phenylpropan-2-yl)-6a,7,8,9,10,10a-hexahydro-6H-isochromeno[3,4-b]pyridin-1-ol.

\* \* \* \* \*

UNITED STATES PATENT AND TRADEMARK OFFICE
CERTIFICATE OF CORRECTION

PATENT NO.        : 8,476,439 B2
APPLICATION NO.   : 13/405642
DATED             : July 2, 2013
INVENTOR(S)       : Bob M. Moore, II, Steven Gurley and Suni Mustafa Page 1 of 1

It is certified that error appears in the above-identified patent and that said Letters Patent is hereby corrected as shown below:

In the claims:

Claim 1, Column 18, line 23

"$C(CH_3)_2$, $C(-U(CH_2),U-)$ and $C(O)$;" should read --$C(CH_3)_2$, $C(-U(CH_2)_n U-)$ and $C(O)$;--.

Claim 1, Column 18, line 31

"substituted up to three tunes and the ring portion of" should read --substituted up to three times and the ring portion of--.

Signed and Sealed this
Twentieth Day of May, 2014

Michelle K. Lee
*Deputy Director of the United States Patent and Trademark Office*